United States Patent [19]

Baiocchi

[11] 4,256,639

[45] Mar. 17, 1981

[54] PROCESS FOR THE SYNTHESIS OF ISATIN DERIVATIVES

[75] Inventor: Leandro Baiocchi, Rome, Italy

[73] Assignee: Aziende Chimiche Riunite Angelini Francesco, Rome, Italy

[21] Appl. No.: 45,792

[22] Filed: Jun. 5, 1979

[30] Foreign Application Priority Data

Jun. 23, 1978 [IT] Italy ................................ 24917 A/78

[51] Int. Cl.³ ................. C07D 209/34; C07D 209/38; C07C 99/06
[52] U.S. Cl. ................................. 260/325 R; 562/456
[58] Field of Search ..................................... 260/325 R

[56] References Cited

U.S. PATENT DOCUMENTS

| 310,604 | 1/1885 | Meyer | 260/325 |
| 3,395,156 | 7/1968 | Wolf | 260/325 |

*Primary Examiner*—Alton D. Rollins
*Attorney, Agent, or Firm*—Ladas & Parry

[57] ABSTRACT

Process for the preparation of the 2-(2,6-dichloroanilino)-phenylacetic acid which comprises, as a basic step, the heating of a mixture containing a pyridic base, an organic or inorganic acid and 4,5,6,7-tetrahydro-N-(2,6-dichlorophenyl)-isatin or its O-acyl or O-alkyl derivatives.

2 Claims, No Drawings

PROCESS FOR THE SYNTHESIS OF ISATIN DERIVATIVES

SUMMARY OF THE INVENTION

According to the present invention, it has been found that the 2-(2,6-dichloroanilino)-phenylacetic acid may be prepared according to the following scheme:

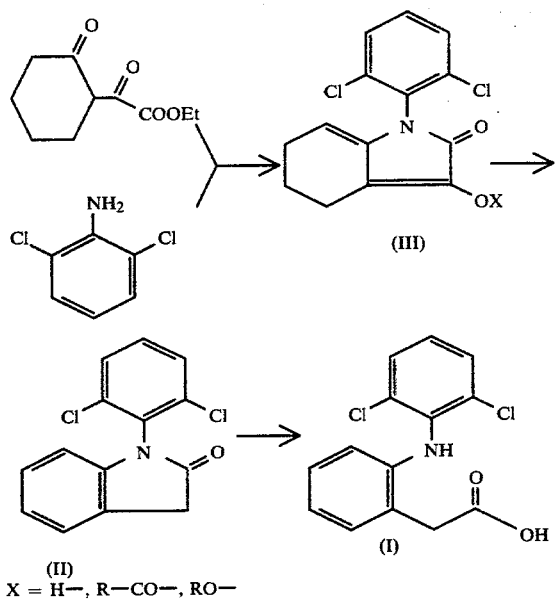

(II)
X = H—, R—CO—, RO—

STATE OF THE ART

During the last years, the 2-(2,6-dichloroanilino)-phenylacetic acid (I) has been successfully introduced in therapy as an antirheumatic and antiphlogistic agent, in its free form or in the form of its sodium salt. Various chemical processes have been described for the preparation thereof. For example, in South African Pat. No. 67/5987, there is reported a synthesis by which the chloroacetyl derivative of the N-benzyl-2,6-dichloroaniline is treated with aluminium trichloride. There is thus obtained the cyclic lactam of the desired acid (II), which is then hydrolized by standard techniques. Such ring closure by the use of aluminium trichloride, according to what is reported in another patent (Ger. Offen. No. 1,815,802), causes the formation of various secondary transition products.

In this second patent there is described, in fact, an alternate synthesis in which the N-benzyl-2,6-dichloroaniline is changed into its corresponding isatin by means of oxalyl chloride. The isatin is then reduced with hydrazine hydrate through a classical Wolff-Kishner reaction to give the product (II).

The process of latter patent, aside from the inconvenient caused by the use of the oxalyl chloride and of the hydrazine hydrate (reactants which are both substantially toxic), has in common with the first and with the other alternate processes (such, for example, the process described in Japanese Pat. No. 46104/1967), the use of the N-benzyl-2,6-dichloroaniline, compound which, because of the low reactivity of the amine group of the 2,6-dichloroaniline, is prepared by means of reactions carried out at high temperatures, over very long reaction periods and with very low yields.

OBJECT OF THE INVENTION

Object of the invention is a completely new and improved method for the preparation of the 2-(2,6-dichloroanilino)-phenylacetic acid from mixtures of a pyridic base, an organic or inorganic acid and the 4,5,6,7-tetrahydro-N-(2,6-dichlorophenyl)-isatine or its simple derivatives.

DETAILED DESCRIPTION OF THE INVENTION

More specifically, it has been found that a compound corresponding to formula (III) may be transformed into a compound (II) by heating in the presence of a salt of a pyridic base. The salt used may be selected among various organic or inorganic acids and among the various pyridic bases; one of the two components may also be in excess with respect to the other. Depending on the particular salt used there are obtained variable reaction times, temperature, yield and quality of the final product. The choice of the particular salt must thus take in consideration the related factors such as availability of the salt, cost and reactivity of the two components, as well as the ease of recovery of the resulting product from the reaction mixture. However, a particular favorable choice has been the utilization of a mixture of adipic acid and pyridine, even if such choice is not to be considered as a limiting factor. In fact, positive results may be obtained also with pyridine hydrochloride, quinoline hydrobromide, lutidine adipate and the like.

The optimal temperature and heating time depend both on the particular derivative of the general formula (III) which is utilized, and on the nature of the acid and the pyridic base. Furthermore, they are interdependent one from the other, since, for example, to a higher reaction temperature corresponds a lower heating time and vice versa.

The choice of the two parameters on the base of an effective convenience in further dependent on the apparatus used. In practice, it has been found that a reaction period of 3 hours (when one operates with III, where X=H) and a temperature of 220° C., or a reaction period of ½ hour (when one operates with III, where X=COCH₃) and a temperature of 230° C. are sufficient for the completion of the reaction. It is to be also taken in consideration that the aforementioned reaction times do not take into consideration the time used in the initial heating of the reaction mixture, which is extremely variable in function of the apparatus used and of the actual quantity of the reaction mixture. Thus said quantities may be considered indicative and not limitative.

As far as regards the nature of X in the formula III, it can be hydrogen, acyl or alkyl.

Also at this point the choice is dictated by various factors, since the tetrahydro-isatin is the most available compound while, in order to obtain the acyl or alkyl derivatives thereof, it is necessary to effect an additional reaction for their preparation. On the other hand, however, said acyl and alkyl derivatives react at a higher reaction speed than the unsubstituted tetrahydro-isatin. In addition, among the various acyl derivatives, there are preferred those which are obtainable from more economical reactants and which can be more easily used. In a particularly preferred embodiment of the invention, there was used the acetyl derivative of the tetrahydro-isatin, which is easily obtainable by heating the product III (X=H) to the boiling point with acetic anhydride. Once the aforementioned boiling operation is ended, the resulting reaction mixture is taken up with water, which dissolves the salt and the eventual excess of the acid or bases utilized.

The residue, which contains the lactam of the 2-(2,6-dichloroanilino)-phenylacetic acid is then hydrolized to the corresponding acid.

It has also unexpectedly been found that the addition of 1% by weight of sodium sulphite to the alkaline solutions used to effect the aforementioned hydrolysis raises the yield of said reaction by about 5%, and additionally yields a product of higher titer.

Such action is somewhat specific and is not effected by other anti-oxidizing agents such as hydroquinone and sodium hydrosulphite.

The 4,5,6,7-tetrahydro-N-(2,6-dichlorophenyl)-isatin needed for the reaction is prepared by the condensation of the 2,6-dichloroaniline with the ethyl 2-cyclohexanone glyoxylate. The 4,5,6,7-tetrahydro-isatin analogues described in the literature, such as the 4,5,6,7-tetrahydro-N-phenyl-isatine (J.A.C.S., 75, 4060 (1953)), are obtained by hydrolysis of the corresponding anil.

The reaction may be carried out with equimolecular quantities of ethyl 2-cyclohexanone-glyoxylate and 2,6-dichloroaniline or with an excess of the latter reactant. In this case, the utilization of the 2-cyclohexanone-glyoxylate results more efficient and further it results easier to recover the unreacted aniline by a simple steam distillation. In a particularly useful variation, at least on a lab scale, there have been used 2,6 mols of aniline for each mole of 2-cyclohexanone-glyoxylate.

Also for this operation, as for the operations already described, there is to be kept in consideration that the various parameters (temperature, reaction, time, molar proportions, nature of the solvents and of the catalysts) may be varied within wide limits without, for this reason, changing the basic essence of the invention. Said parameters must be taken in consideration in order to optimize the costs, the investments, the productivity and the work safety for each single productive installation.

The examples, which follow, and which illustrate the invention, are not limitative and relate to solutions which have been particularly effective on a bench scale.

EXAMPLE 1

4,5,6,7-tetrahydro-N-(2,6-dichlorophenyl)-isatin

A solution of 65 g (0.33 mols) of ethyl 2-cyclohexanone-glyoxylate and 135 g (0.83 mols) of 2,6-dichloroaniline in 150 ml of methanol is refluxed for 30 hours. After this period, there is introduced steam into the reaction vessel, thus removing the excess 2,6-dichloroaniline. The residue of the steam distillation is removed by filtration and recrystallized from methanol.

Yield: 30 g (31%); m.p. 251°–253° C.

Sodium salt of the 2-(2,6-dichloroanilino)-phenylacetic acid

In a cooled round bottom distillation flask there are added 70 g (0.24 mols) of the preceding product, 714 ml (9 mols) of pyridine and 650 g (4.5 mols) of adipic acid. The mixture is heated rapidly with stirring up to an internal temperature of 230° C. and kept at this temperature for three hours. During this period, most of the pyridine is removed by distillation. The resulting reaction mixture is allowed to cool to about 100° C. and is then poured into 1500 ml of water. The mixture is filtered at 60° C. and the residue is again washed with 1500 ml of water at 60° C. The residue is suspended in a water-alcohol solution obtained by mixing 600 ml of NaOH (1 N) in 900 ml of 95° ethanol and adding 6 g of Na$_2$SO$_3$.

After 2.5 hours of refluxing, the alcohol is removed under reduced pressure. On cooling of the remaining aqueous solution, there separates therefrom the sodium salt of the 2-(2,6-dichloroanilino)-phenylacetic acid, which is removed by filtration and eventually recrystallized from water; m.p. 282°–285° C. The melting point reported in the literature (Germ. Offen. No. 1,815,802) is 281°–283° C.

EXAMPLE 2

Acetyl derivative of the 4,5,6,7-tetrahydro-N-(2,6-dichlorophenyl)-isatin

There are dissolved in 500 ml of acetic anhydride 87 g (0.29 mols) of 4,5,6,7-tetrahydro-N-(2,6-dichlorophenyl)isatin. The solution is refluxed for 2 hours and the excess acetic anhydride is removed by heating on a steam bath under reduced pressure. The residue is taken up in one liter of water and the solid which separates is filtered and washed with 95° alcohol;

Yield: 93 g (93.5%); m.p.: 160°–161° C.

Lactam of the 2-(2,6-dichloroanilino)-phenylacetic acid

A mixture of 30 g (0.089 mols) of the preceding product, 150 ml (1.86 mols) of pyridine and 150 g (0.96 mols) of adipic acid are heated as described in Ex. 1. After one half hour of heating at the maximum temperature (230° C.), the mixture, still hot, is poured into 1000 ml of water. The solid which separates is washed by decantation with another 1000 ml of water at 60° C. and then recrystallized from methanol.

Yield: 16 g (64.5%); m.p.: 122°–124° C.

2-(2,6-dichloroanilino)-phenylacetic acid

To a solution obtained by admixing 42 ml of 1 N NaOH, 0.42 g of Na$_2$SO$_3$ and 65 ml of 95° ethanol, there is added 6 g (0.022 mols) of the preceding product. The mixture is then refluxed for 2 hours and the alcohol is then removed under reduced pressure. The mixture is diluted with 150 ml of water, the solution is acidified and the acid, which precipitates, is removed by filtration.

The product may be recrystallized from isopropyl ether. The melting point is 164°–167° C. The reported melting point (South African Pat. No. 67/5987) is 156°–158° C.

EXAMPLE 3

3-0-methyl derivative of the enolic form of the 4,5,6,7-tetrahydro-N-(2,6-dichlorophenyl)-isatin A suspension of 30 g of 4,5,6,7-tetrahydro-N-(2,6-dichlorophenyl)-isatin (0.1 mols) in 300 ml of methanol is saturated with gaseous HCl, while cooling the reaction mixture with an ice-water mixture. The resulting solution, after it is allowed to rest for one night, is poured into 1500 ml of an ice-water mixture. The solid thus obtained is filtered and is air-dried.

Yield: 26 g (83%); m.p.: 134°–137° C.

Lactam of the 2-(2,6-dichloroanilino)-phenylacetic acid

A mixture of 250 ml (3.2 mols) of pyridine, 230 g (1.57 mols) of adipic acid and 25 g (0.08 mols) of the preceding product is heated for one hour at 230° C.

At the end of the heating cycle, the resulting mixture is treated as described in Example 1.

There is obtained 12 g (Yield 54%, m.p.: 123°–125° C.) of the lactam of the 2-(2,6-dichloroanilino)-phenylacetic acid which is hydrolyzed as described in Example 2.

What is claimed is:

1. A method for preparing the lactam of 2-(2,6-dichloroanilino)-phenylacetic acid wherein 4,5,6,7-tetrahydro-N-(2,6-dichlorophenyl)-isatin of the formula:

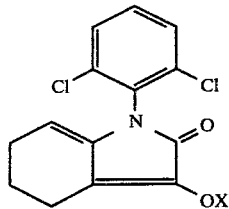

wherein X is hydrogen, lower alkanoyl or lower alkyl, is heated in the presence of an organic or inorganic acid and pyridine, quinoline or lutidine, and the resulting product is purified by crystallization.

2. A method according to claim 1 wherein X is acetyl.

* * * * *